US005677168A

United States Patent [19]
Zard et al.

[11] Patent Number: 5,677,168
[45] Date of Patent: Oct. 14, 1997

[54] ENANTIOMERIC SEPARATION OF (RS)1-(4-CHLOROPHENYL)-2-CHLOROETHANOL BY LIPASE CATALYZED HYDROLYSIS OF ITS ACETATE

[75] Inventors: Lydia Zard, Gif sur Yvette; Arlette Tixidre, Orsay, both of France

[73] Assignee: Synthelabo, Le Plessis Robinson, France

[21] Appl. No.: 575,956

[22] Filed: Dec. 22, 1995

[30] Foreign Application Priority Data

Dec. 23, 1994 [FR] France .................... 94 15548

[51] Int. Cl.$^6$ .................................... C12P 41/00
[52] U.S. Cl. .................. 435/280; 435/156; 435/874; 435/921
[58] Field of Search ............... 435/280, 156, 435/921, 874

[56] References Cited

U.S. PATENT DOCUMENTS 5,312,950  5/1994  Boaz ............................. 558/51

FOREIGN PATENT DOCUMENTS

| 0 493 617 | 7/1992 | European Pat. Off. . |
| 2696741 | 4/1994 | France . |
| WO92/14830 | 9/1992 | WIPO . |

OTHER PUBLICATIONS

Langrand G et al., Lipase Catalyzed Reactions and Strategy for Alcohol Resolution, Tet. Lett. 27:29–32 (1986).

Nieduzak, T.R. et al, "Multigram lipase–catalyzed enantiose–selective acylation in the synthesis of the four stereoisomers of a new biologically active alpha–aryl–4–piperidinemethanol derivative", Tetrahedron: Asymmetry, vol. 2, No. 2, 1991, pp. 113–122.

Kutsuki, H. et al, "Asymmetric hydrolysis of (dl)–1–acyloxy–2–halo–1–phenylethanes with lipase", Agric. Biol. Chem., vol. 50, No. 9, 1986, pp. 2369–2373.

Woodcock, D., "Insecticidal activity and chemical constitution Part I. Chlorinated p–chloroethylbenzene", Journal of the Chemical Society, 1949, pp. 203–207.

*Primary Examiner*—Sandra E. Saucier
*Attorney, Agent, or Firm*—Jacobson, Price, Holman & Stern, PLLC

[57] ABSTRACT

Process for the preparation of one or both enantiomers of 1-(4-chlorophenyl)-2-chloroethanol, which comprises an enantioselective enzymatic hydrolysis of (±)-α-(4-chlorophenyl)chloroethyl acetate by means of an enzyme which is horse liver acetone powder, lipase PS from *Pseudomonas fluorescens*, lipase AK from Pseudomonas or the lipase from *Candida antarctica*, to give a mixture of unhydrolysed R-(−)-α-(4-chlorophenyl)chloroethyl acetate and S-(+)-1-(4-chlorophenyl)-2-chloroethanol, and optional separation of R-(−)-α-(4-chlorophenyl)chloroethyl acetate and optional hydrolysis of it to give R-(−)-1-(4-chlorophenyl)-2-chloroethanol and use of the enantiomers of 1-(4-chlorophenyl)-2-chlorethanol for the preparation of the enantiomers of eliprodil and of their salts.

7 Claims, No Drawings

ENANTIOMERIC SEPARATION OF (RS)1-(4-CHLOROPHENYL)-2-CHLOROETHANOL BY LIPASE CATALYZED HYDROLYSIS OF ITS ACETATE

The present invention relates to a process for the preparation of the enantiomers of 1-(4-chlorophenyl)-2-chloroethanol and their use in the preparation of the enantiomers of eliprodil and of their salts.

Eliprodil or α-(4-chlorophenyl)-4-[(4-fluorophenyl) methyl]piperidine-1-ethanol of formula

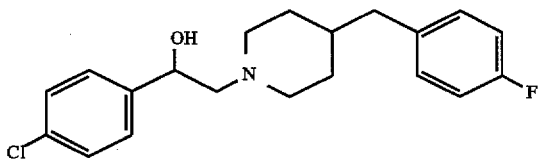

is a known compound which is described, along with its neuroprotective properties, in European Patent No. 0,109,317.

A process for the preparation of its enantiomers is described in the utility certificate FR 89 04835.

The present invention provides a process for the preparation of one or both enantiomers of 1-(4-chlorophenyl)-2-chloroethanol, which comprises an enantioselective enzymatic hydrolysis of (±)-α-(4-chlorophenyl)chloroethyl acetate, to give a mixture of unhydrolysed R-(−)-α-(4-chlorophenyl)chloroethyl acetate and of S-(+)-1-(4-chlorophenyl)-2-chloroethanol, then the optional separation of the constituents of the mixture, optionally after conversion of S-(+)-1-(4-chlorophenyl)-2-chloroethanol to S-(+)-α-(4-chlorophenyl)chloroethyl succinate, and the optional hydrolysis of R-(−)-α-(4-chlorophenyl)chloroethyl acetate and of S-(+)-α-(4-chlorophenyl)chloroethyl succinate if present.

According to the invention, the hydrolysis of (±)-α-(4-chlorophenyl)chloroethyl acetate is generally carried out in a buffered aqueous medium, for example a phosphate buffer solution containing a mixture of potassium diphosphate and of disodium phosphate, or in a two-phase medium consisting of a buffer solution and of an organic solvent, such as toluene, hexane or t-butyl methyl ether.

The enzyme used for the selective hydrolysis of (±)-α-(4-chlorophenyl)chloroethyl acetate to S-(+)-1-(4-chlorophenyl)-2-chloroethanol is horse liver acetone powder (marketed by Sigma), lipase PS from *Pseudomonas fluorescens* (marketed by Amano), lipase AK from Pseudomonas (marketed by Amano) or the supported or nonsupported lipase from *Candida antarctica* (Novozym® SP 435 and SP 525 respectively, marketed by Novo).

The enzyme, in the free form or else immobilized on a support, is generally used at a concentration of from 3 to 50% by weight with respect to the weight of (±)-α-(4-chlorophenyl)chloroethyl acetate.

The constituents of the mixture of R-(−)-α-(4-chlorophenyl)chloroethyl acetate and of S-(+)-1-(4-chlorophenyl)-2-chloroethanol can be separated by chromatography.

The mixture of R-(−)-α-(4-chlorophenyl)chloroethyl acetate and of S-(+)-1-(4-chlorophenyl)-2-chloroethanol can also be treated with, for example, succinic anhydride, to give a mixture of R-(−)-α-(4-chlorophenyl)chloroethyl acetate and of S-(+)-α-(4-chlorophenyl)chloroethyl succinate. After treatment with a base, such as sodium hydroxide, the S-(+)-α-(4-chlorophenyl)chloroethyl succinate, in the salt form, is extracted into an aqueous phase and the R-(−)-α-(4-chlorophenyl)chloroethyl acetate is extracted into an organic phase. By acidification of the medium containing the salt of S-(+)-α-(4-chlorophenyl)chloroethyl succinate and extraction into an organic phase, S-(+)-α-(4-chlorophenyl) chloroethyl succinate is obtained.

R-(−)-1-(4-chlorophenyl)-2-chloroethanol and S-(+)-1-(4-chlorophenyl)-2-chloroethanol are then respectively obtained by hydrolysis of R-(−)-α-(4-chlorophenyl) chloroethyl acetate and of S-(+)-(4-chlorophenyl) chloroethyl succinate.

The present invention also provides the use of the enantiomers of 1-(4-chlorophenyl)-2-chloroethanol with 4-[(4-fluorophenyl)methyl]-piperidine for the preparation of the enantiomers of eliprodil or a salt thereof.

The enantiomers of eliprodil can then be converted to acid addition salts by treatment with inorganic or organic acids, according to processes known per se.

The (±)-α-(4-chlorophenyl)chloroethyl acetate used as starting material in the process of the invention is generally prepared by reduction of 2-chloro-1-(4-chlorophenyl) ethanone and acetylation of the (±)-1-(4-chlorophenyl)-1-chloroethanol thus obtained, according to the scheme represented in Appendix 1.

The general scheme for the synthesis of the enantiomers of 1-(4-chlorophenyl)-2-chloroethanol from (±)-α-(4-chlorophenyl)chloroethyl acetate according to the process of the invention is represented in Appendix 2.

The scheme for the synthesis of the enantiomers of eliprodil and of their hydrochlorides from the enantiomers of 1-(4-chlorophenyl)-2-chloroethanol is represented in Appendix 3.

The following examples illustrate the present invention, Examples 1 to 7 relating to the preparation of the enantiomers of 1-(4-chlorophenyl)-2-chloroethanol or of their synthetic intermediates according to the process of the invention and Examples 8 to 12 relating to the application to the preparation of the enantiomers of eliprodil and of their hydrochlorides.

EXAMPLE 1

R-(−)-α-(4-chlorophenyl)chloroethyl acetate and S-(+)-1-(4-chlorophenyl)-2-chloroethanol 1.1 (±)-α-(4-chlorophenyl)chloroethyl acetate A solution of 100 g (0.54 mol) of 1-(4-chlorophenyl)-2-chloroethanone in 600 ml of methanol is cooled with an ice bath and then 7.6 g (0.2 mol) of sodium borohydride are added slowly, under argon and with stirring, the temperature of the reaction mixture being maintained below 15° C. The mixture is then stirred for 2 h at room temperature, the methanol is then evaporated, the residue is poured into ice-cold water, which is acidified with a 10% aqueous hydrochloric acid solution, and extraction is carried out with 3 times 300 ml of dichloromethane. The organic phases are combined and dried over magnesium sulphate and the solvent is evaporated under vacuum. The residue is taken up in 400 ml of dichloromethane and 43 ml of pyridine, the solution is cooled with an ice bath and 42 ml (0.59 mol) of acetyl chloride are added dropwise. Heating is then carried out at reflux for 2 h, the reaction mixture is then filtered and the filtrate is washed with water. The organic phase is dried, filtered and the solvent evaporated under vacuum. 116 g of product are obtained in the form of an oil.

1.2 R-(−)-α-(4-chlorophenyl)chloroethyl acetate and S-(+)-1-(4-chlorophenyl)-2-chloroethanol 40 g of (±)-α-(4-chlorophenyl)chloroethyl acetate are suspended in 500 ml of a 0.01M phosphate buffer solution, consisting of potassium biphosphate and of disodium phosphate, at 21° C., the pH is then adjusted to 7.2 by addition of an aqueous hydrochloric acid solution and 4 g of lipase AK are added. Reaction is allowed to take place for 76 h, the pH being kept constant by addition of a 1M aqueous sodium hydroxide solution, and then the aqueous phase is extracted with 4 times 300 ml of dichloromethane. The organic phases are combined, dried over magnesium sulphate and filtered and the solvent is evaporated under vacuum. 34 g of an oily product are obtained, which product consists of a mixture of R-(−)-α-(4-chlorophenyl) chloroethyl acetate and of S-(+)-1-(4-chlorophenyl)-2-chloroethanol. By chromatography on a silica column with a 95/5 mixture of cyclohexane and ethyl acetate, the following are obtained:

13.85 g of S-(+)-1-(4-chlorophenyl)-2-chloroethanol $[\alpha]_D^{20}$=+43.8° (c=0.974, chloroform)

ee: 100% [chiral HPLC: covalent phenylglycine (Pirkle), 230 nm, 0.6 ml/mn, hexane/isopropanol (99/1)], and 15 g of R-(−)-α-(4-chlorophenyl)chloroethyl acetate $[\alpha]_D^{20}$=−64.7° (c=1.17, chloroform)

ee>98% (chiral HPLC, same conditions as above).

EXAMPLE 2

R-(−)-α-(4-chlorophenyl)chloroethyl acetate and S-(+)-1-(4-chlorophenyl)-2-chloroethanol According to the process of Stage 2 of Example 1, from 20 g of (±)-α-(4-chlorophenyl)chloroethyl acetate, 350 ml of phosphate buffer and 6 g of lipase PS from *Pseudomonas fluorescens*, which are reacted for 42 h, the following are obtained after chromatography: 9 g of R-(−)-α-(4-chlorophenyl)chloroethyl acetate (ee: 99%) and 6.95 g of S-(+)-1-(4-chlorophenyl)-2-chloroethanol (ee>98%).

EXAMPLE 3

R-(−)-α-(4-chlorophenyl)chloroethyl acetate and S-(+)-1-(4-chlorophenyl)-2-chloroethanol According to the process of Stage 2 of Example 1, 20 mg of (±)-α-(4-chlorophenyl)chloroethyl acetate are treated in 0.5 ml of phosphate buffer with 2 mg of Novozym® SP 525 and the progress of the reaction is monitored by chiral HPLC. After 24 h, the following are found: ee>97% for R-(−)-α-(4-chlorophenyl)chloroethyl acetate and for S-(+)-1-(4-chlorophenyl)-2-chloroethanol.

EXAMPLE 4

R-(−)-α-(4-chlorophenyl)chloroethyl acetate and S-(+)-1-(4-chlorophenyl)-2-chloroethanol According to the process of Stage 2 of Example 1, 6 g of (±)-α-(4-chlorophenyl)chloroethyl acetate are treated in 75 ml of phosphate buffer with 600 mg of Novozym® SP 435 and the progress of the reaction is monitored by chiral HPLC. After 3 days, the reaction mixture is diluted with 50 ml of dichloromethane and then filtered. The aqueous phase is then extracted with 3 times 50 ml of dichloromethane and the organic phases are combined, dried and concentrated under reduced pressure in order to obtain 5.34 g of product in the form of an oil. The residue is taken up in a small amount of cyclohexane and is then chromatographed on a silica column, first with a 99/1 mixture, then with a 90/10 mixture, of cyclohexane and ethyl acetate. 2.66 g of R-(−)-α-(4-chlorophenyl)chloroethyl acetate (ee=86%) and 2.06 g of S-(+)-1-(4-chlorophenyl)-2-chloroethanol (ee=97%) are obtained.

EXAMPLE 5

R-(−)-α-(4-clorophenyl)chloroethyl acetate and S-(+)-α-(4-chlorophenyl)chloroethyl succinate 40 l of demineralized water, 44.5 g of disodium hydrogenphosphate dihydrate, 20.4 g of potassium dihydrogenphosphate and 2382 g of (±)-α-(4-chlorophenyl)chloroethyl acetate are introduced into a 50 l reactor and the pH is adjusted to 7.2 by addition of a 1M sodium hydroxide solution. 92.7 g of lipass SP 525 are then added, with stirring, and a 1M sodium hydroxide solution is injected so as to maintain the pH at 7.0±0.2.

After 48 hours, after addition of 4.5 l of sodium hydroxide, the suspension is extracted with a mixture of 25 l of toluene and 35 l of ethanol and then with a mixture of 25 l of toluene and 15 l of ethanol. The upper organic phases are combined and evaporated to dryness, the residue is taken up in 10 l of t-butyl methyl ether and 3 kg of sodium sulphate, filtration is then carried out, the sulphate is rinsed with 5 l of t-butyl methyl ether and the ethereal solution is evaporated to dryness. There are thus obtained 1927 g of a mixture, in the form of an oil, containing R-(−)-α-(4-chlorophenyl)chloroethyl acetate (ee=99.06%) and S-(+)-1-(4-chlorophenyl)-2-chloroethanol (ee=86.0%).

This mixture is dissolved in 11 l of toluene and then 641 g of triethylamine and 634 g of succinic anhydride are added. The mixture is left stirring at room temperature overnight and then the acid compounds are extracted with a solution of 530 ml of 30% sodium hydroxide in 6 l of demineralized water. After separation by settling, the toluene phase is re-extracted with 3 l of demineralized water and the aqueous phases are then combined and washed with 3 l of toluene.

The toluene phases are combined and evaporated to dryness and then the 1189 g of product obtained are dissolved in hexane. After absorption on 1.75 kg of silica, elution with 1 l of hexane, 4 l of a 90/10 mixture, 3 l of an 80/20 mixture and 1 l of a 50/50 mixture of hexane and ethyl acetate, and evaporation of the solvent, 1056 g of R-(−)-α-(4-chlorophenyl)-chloroethyl acetate are obtained.

The basic aqueous phases are combined and then acidified by addition of 36% hydrochloric acid to pH=5. The acid succinate is then extracted with 2×2 l of dichloromethane, the solvent is evaporated and the 1405 g of oily residue obtained are redissolved in dichloromethane. After absorption on 2 kg of silica and elution with 4 l of dichloromethane, 2 l of a 90/10 mixture and 2 l of a 50/50 mixture of dichloromethane and methanol, and then 1 l of methanol, and evaporation of the solvent, 1349 g of S-(+)-α-(4-chlorophenyl)chloroethyl succinate are obtained in the form of an oil.

EXAMPLE 6

S-(+)-1-(4-chlorophenyl)-2-chloroethanol 530 g of acetyl chloride are added over 1 hour, while maintaining the temperature below 6° C., to a solution of 1340 g of S-(+)-α-(4-chlorophenyl)chloroethyl succinate in 7.5 l of methanol cooled to 0° C. The mixture is then heated at reflux for 9 hours and is then concentrated to dryness under reduced pressure. 1053 g of a mixture of S-(+)-1-(4-chlorophenyl)-2-chloroethanol and of dimethyl succinate are obtained.

$[\alpha]_d^{20}$ of the mixture=+23.6° (c=1, chloroform)

ee=86.6% (chiral HPLC).

EXAMPLE 7

R-(−)-1-(4-chlorophenyl)-2-chloroethanol 1050 g of R-(−)-α-(4-chlorophenyl)chloroethyl acetate are dissolved in 7 l of methanol, the reaction mixture is then cooled in an ice bath and 460 g of acetyl chloride are added over 1 hour, the temperature being maintained below 5° C. The reaction mixture is then heated at 50° C. for 1 h and then concentrated to dryness. 820 g of product are obtained.

$[\alpha]_D^{20}$=−47.2° (c=1, chloroform).
ee=97.7%.

EXAMPLE 8

S-(+)-α-(4-chlorophenyl)-4-[(4-fluorophenyl)methyl]-piperidine-1-ethanol 19 g (0.1 mol) of S-(+)-1-(4-chlorophenyl)-2-chloroethanol, obtained according to one of Examples 1 to 3, are dissolved in 230 ml of isopropanol and then 33 ml of water, 16.35 g (0.12 mol) of potassium carbonate and 22.5 g (0.1 mol) of 4-[(4-fluorophenyl)-methyl]piperidine are added. The reaction mixture is heated at reflux for 3 h, is then allowed to return to room temperature and the precipitate formed is filtered off and dried. The solid residue is taken up in water and the insoluble product is then filtered off, dried and recrystallized from 350 ml of absolute ethanol at reflux.

20.2 g of product are obtained.
Melting point: 142°–143° C.
$[\alpha]_D^{20}$=+47.9° (c=1.015, chloroform)
ee>99.8% (chiral HPLC).

EXAMPLE 9

S-(+)-α-(4-chlorophenyl)-4-[(4-fluorophenyl)methyl]-piperidine-1-ethanol 5 l of isopropanol, 0.93 l of water, 851 g of potassium carbonate, 643 g of 4-[(4-fluorophenyl)methyl]-piperidine hydrochloride and 978 g of the mixture of S-(+)-1-(4-chlorophenyl)-2-chloroethanol and of dimethyl succinate obtained according to Example 6 are introduced into a 10 l reactor maintained under nitrogen. 1.4 l of isopropanol are added and the reaction mixture is then heated at reflux for 4 hours. The suspension is then cooled to 15° C. and is filtered, the solid is then rinsed with 1 l of isopropanol and is suspended in 8 l of water, and stirring is carried out for 1 h 15 min. After filtering and washing with water, the solid is dried overnight at 50° C. under reduced pressure. The product obtained is recrystallized from 9.8 l of ethanol. 608 g of product are obtained.

Melting point: 144°–144.3° C.
$[\alpha]_D^{20}$=+46.8° (c=1, chloroform)
ee=99.4%.

EXAMPLE 10

R-(−)-α-(4-chlorophenyl)-4-[(4-fluorophenyl)methyl]piperidine-1-ethanol

From 9.1 g of R-(−)-1-(4-chlorophenyl)-2-chloroethanol and 10.76 g of 4-[(4-fluorophenyl)methyl]piperidine, treated under the conditions of Example 8, 12.2 g of product are obtained.

Melting point: 142°–143° C.
$[\alpha]_D^{20}$=−47.9° (c=1.015, chloroform)
ee>99.8%.

EXAMPLE 11

R-(−)-α-(4-chlorophenyl)-4-[(4-fluorophenyl)methyl]piperidine-1-ethanol hydrochloride 130 ml of concentrated hydrochloric acid are added to a suspension of 495 g of R-(−)-α-(4-chlorophenyl)-4-[(4-fluorophenyl)methyl]-piperidine-1-ethanol in 1.5 l of ethanol and the mixture is heated until dissolved. The solution is then cooled with an ice bath and the precipitate formed is filtered off and rinsed with 0.25 l of ethanol. The 465 g of product obtained are recrystallized from 2 l of ethanol. 415 g of pure product are thus obtained.

Melting point: 216.8° C.
$[\alpha]_D^{20}$=−34° (c=1, methanol)
ee>99.9%.

EXAMPLE 12:

S-(+)-α-(4-chlorophenyl)-4-[(4-fluorophenyl)methyl]piperidine-1-ethanol hydrochloride S-(+)-α-(4-chlorophenyl)-4-[(4-fluorophenyl)methyl]-piperidine-1-ethanol hydrochloride is obtained from S-(+)-α-(4-chlorophenyl)-4-[(4-fluorophenyl)methyl]-piperidine-1-ethanol according to the process described in Example 11.

Melting point: 217.1° C.
$[\alpha]_D^{20}$=+34.7° (c=1, methanol)
ee=99.4%.

Appendix 1

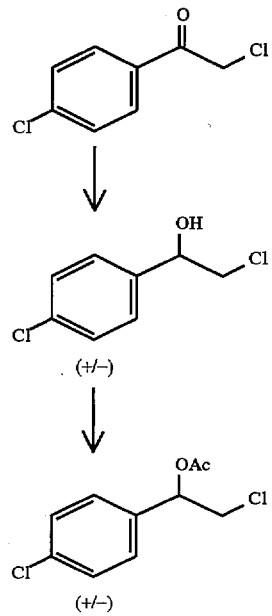

Appendix 2
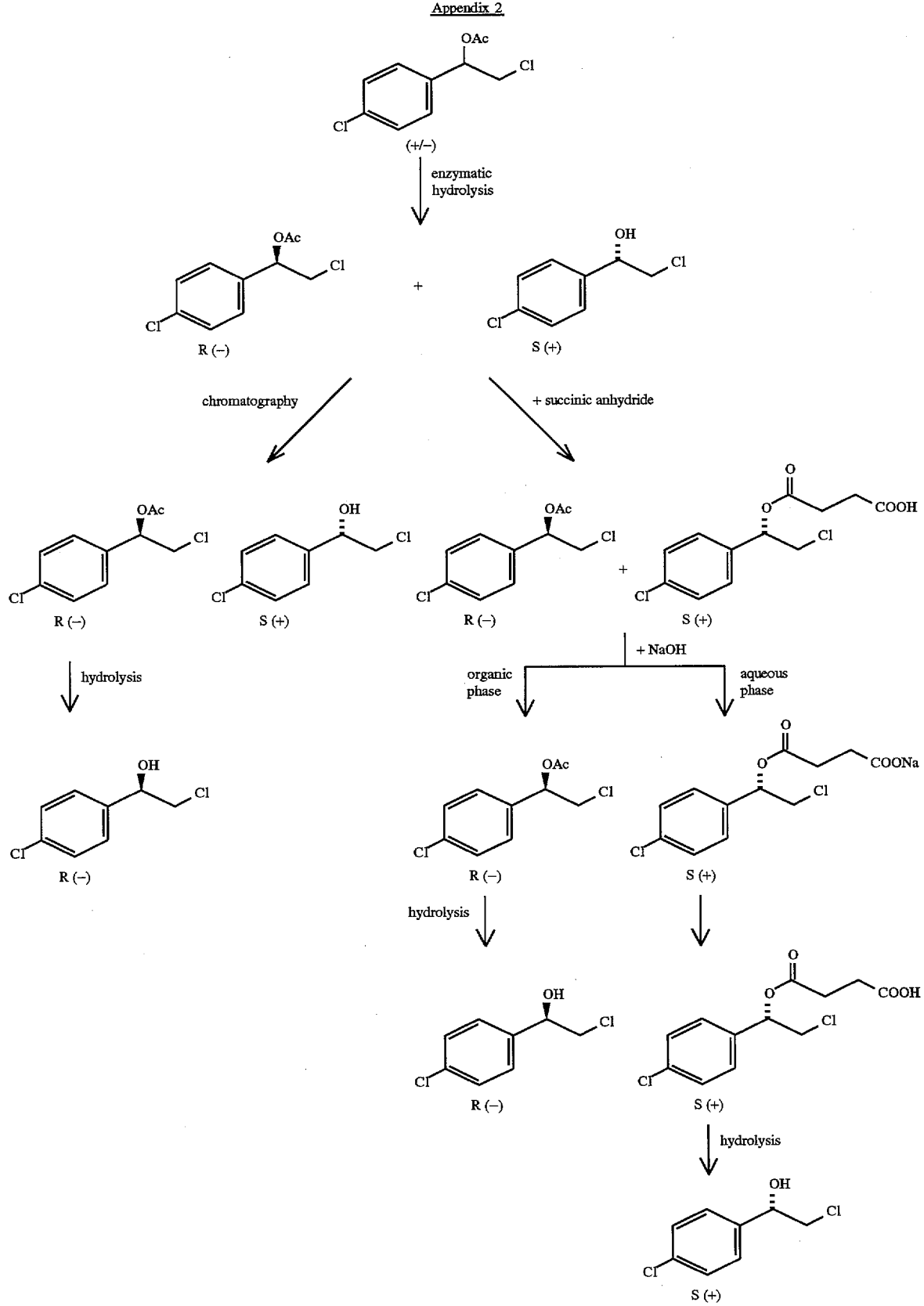

Appendix 3

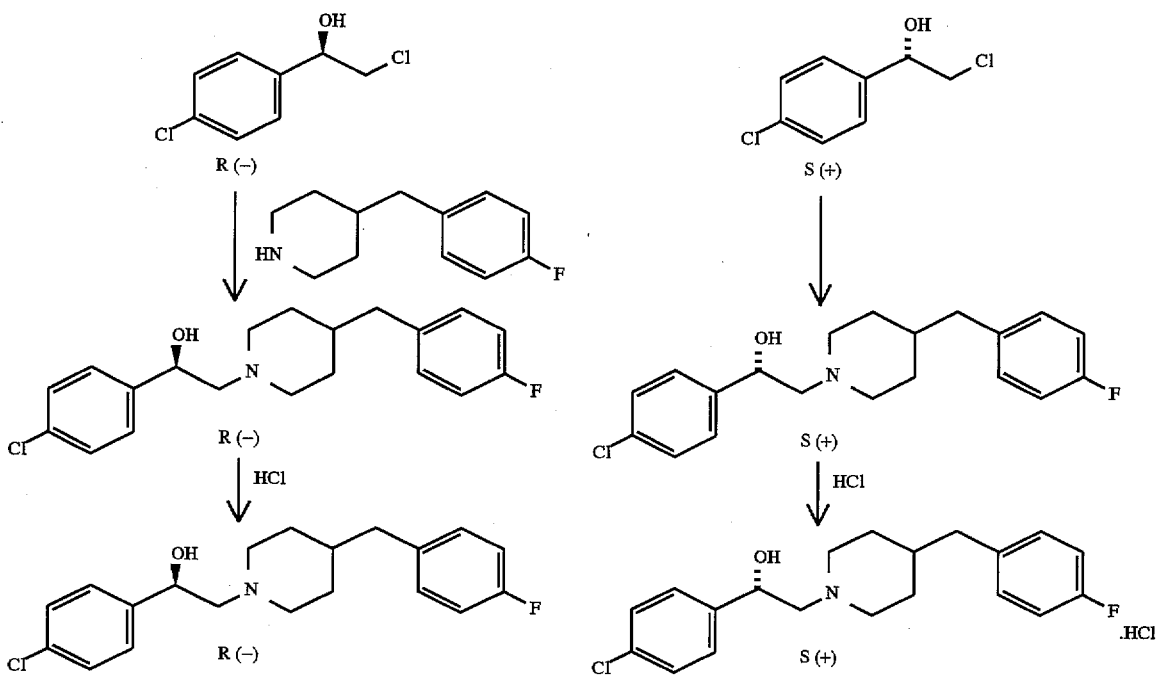

We claim:

1. A process for the preparation of one or both enantiomers of 1-(4-chlorophenyl)-2-chloroethanol, comprising subjecting (±)-α-(4-chlorophenyl)chloroethyl acetate to an enantioselective enzymatic hydrolysis using an enzyme selected from the group consisting of lipase of horse liver acetone powder, lipase AK from Pseudomonas and lipase from *Candida antarctica* to give a mixture of unhydrolyzed R-(−)-α-(4-chlorophenyl)chloroethyl acetate and S-(+)-1-(4-chlorophenyl)-2-chloroethanol.

2. The process according to claim 1 further comprising separating R-(−)-α-(4-chlorophenyl)chloroethyl acetate from the mixture and optionally hydrolyzing it to give R-(−)-1-(4-chlorophenyl)-2-chloroethanol.

3. The process according to claim 2 in which the separation of R-(−)-α-(4-chlorophenyl)chloroethyl acetate is by chromatography and the R-(−)-α-(4-chlorophenyl)chloroethyl acetate is hydrolyzed.

4. The process according to claim 1 further comprising converting the S-(+)-1-(4-chlorophenyl)-2-chloroethanol in the mixture to S-(+)-α-(4-chlorophenyl)-2-chloroethyl succinate and separating it from the mixture and then hydrolyzing it after the separation.

5. The process according to claim 4 in which the conversion is carried out with succinic anhydride and the separation of S-(+)-α-(4-chlorophenyl)chloroethyl succinate from R-(−)-α-(4-chlorophenyl)chloroethyl acetate is carried out by extraction of the S-(+)-α-(4-chlorophenyl)chloroethyl succinate in the salt form into an aqueous phase and of the R-(−)-α-(4-chlorophenyl)chloroethyl acetate into an organic phase, acidifying the salt form of the S-(+)-α-(4-chlorophenyl)chloroethyl succinate in the aqueous phase and extracting it into an organic phase and hydrolyzing the R-(−)-α-(4-chlorophenyl)chloroethyl acetate.

6. The process according to claim 1 in which the enzyme is immobilized on a support.

7. The process according to claim 1 in which the concentration by weight of enzyme with respect to the weight of (±)-α-(4-chlorophenyl)chloroethyl acetate is from 3 to 50%.

* * * * *